United States Patent [19]

Kenji et al.

[11] Patent Number: 4,492,531
[45] Date of Patent: Jan. 8, 1985

[54] APPARATUS FOR PRODUCING A CONTROLLED PULSED LIQUID FLOW

[75] Inventors: Kubota Kenji, Okayama; Fukunaga Kouji, Kurashiki; Kirita Yasuzo, Toyonaka; Naito Hidemune, Kobe, all of Japan

[73] Assignee: Kuraray Co., Ltd., Kurashiki, Japan

[21] Appl. No.: 487,212

[22] Filed: Apr. 21, 1983

[30] Foreign Application Priority Data

Apr. 30, 1982 [JP] Japan ................... 57-74169

[51] Int. Cl.³ .................. F04B 49/00; F04B 43/12; A61M 1/03; B01D 13/00
[52] U.S. Cl. .................. 417/279; 417/477; 604/5; 604/65; 210/321.3; 210/927
[58] Field of Search ........... 417/279, 280, 290, 317, 417/412, 474–477, 505, 26–28; 604/4, 5, 65, 67; 128/DIG. 3; 210/91, 321.3, 927

[56] References Cited

U.S. PATENT DOCUMENTS

| | | | |
|---|---|---|---|
| Re. 29,346 | 8/1977 | Kopp | 604/5 |
| 3,437,050 | 4/1969 | Hrdina | 417/476 X |
| 3,726,613 | 4/1973 | Von Casimir | 417/477 |
| 3,731,680 | 5/1973 | Wright et al. | 604/5 |
| 3,756,234 | 9/1973 | Kopp | 604/5 |
| 3,758,237 | 9/1973 | Kachelhoffer | 128/DIG. 3 X |
| 3,784,323 | 1/1974 | Sausse | 417/477 X |
| 3,811,800 | 5/1974 | Shill | 417/317 |
| 3,830,234 | 8/1974 | Kopp | 604/5 |
| 3,881,483 | 5/1975 | Sausse | 604/4 |
| 3,985,134 | 10/1976 | Lissot et al. | 604/5 |
| 4,063,554 | 12/1977 | Willock et al. | 604/5 X |
| 4,231,366 | 11/1980 | Schael | 604/4 |
| 4,322,201 | 3/1982 | Archibald | 417/279 |
| 4,357,239 | 11/1982 | Bellhouse et al. | 210/321.3 |

FOREIGN PATENT DOCUMENTS

| 167009 | 12/1980 | Japan | 210/321.3 |
|---|---|---|---|
| 2102503 | 2/1983 | United Kingdom | 417/477 |

Primary Examiner—William L. Freeh
Assistant Examiner—Paul F. Neils
Attorney, Agent, or Firm—Kramer and Brufsky

[57] ABSTRACT

An apparatus designed for supplying liquid by means of a roller pump into a membrane module having membranes provided therein in such a way that liquid is introduced in pulsed state into the membrane module by periodically opening and closing a flow path by means of a valve disposed on the flow path on the inlet side or outlet side of the membrane module. The resistance of the membranes to material transfer is reduced and liquid channelling in the membrane module is reasonably avoided, so that the effective area of each membrane may be increased. The apparatus can be advantageously employed to improve the performance of various blood treating and body cavity fluid treating apparatuses incorporating membranes.

6 Claims, 10 Drawing Figures

APPARATUS FOR PRODUCING A CONTROLLED PULSED LIQUID FLOW

BACKGROUND OF THE INVENTION

1. Field of the Invention

The present invention relates to an apparatus for producing pulses, of the type which is designed for supplying liquid by means of a roller pump into a membrane module having membranes provided therein, in such a way that liquid is introduced in pulsed state into the membrane module by periodically opening and closing a flow path by means of a valve disposed on the flow path on the inlet side or outlet side of the membrane module. The apparatus of the invention may be advantageously employed in blood treating apparatuses such as those for hemodialysis, hemofiltration, and plasmapheresis, and body cavity fluid treating apparatuses such as those for ascitic fluid filtration, ascitic fluid concentration, and pleural fluid concentration.

2. Description of Prior Art

In recent years significant progress has been made in the field of blood treatment, such as hemodialysis, wherein undesirable substances present in the blood of a patient suffering from renal failure or hepatic insufficiency are removed by using a membrane module incorporating dialyzer membranes of hollow fiber shape or flat plate shape. Such progress presents bright prospects for saving or prolongation of patient lives. In order to facilitate the return of patients to normal life and to reduce the time required for such treatment, however, it is essential that the performance of the membrane module be further improved. As a method for improving membrane-module performance, it has recently been proposed to supply blood in pulsed state into the membrane module by using a pulsatile pump (Artificial Organs, Vol. 10, No. 1, pp 85~88, 1981). With roller pumps used for hemodialysis purposes today, it is seen that the rollers move forward while compressing the blood circuit; therefore, it is obvious that pulses, though insignificant, can be applied to the blood. The proposed method, it is said, will permit a reduction of resistance due to material transfer, correction of channelling, and increase of effective membrane area, through supply of blood in a much higher degree of pulsed state than that usually produced by the membrane module and roller pump, so that some 10% improvement can be obtained in hemodialysis efficiency. Furthermore, according to the observation of the present inventors, said method has an additional advantage that in a little anticoagulant hemodialysis as well as in non-anticoagulant hemolysis, blood coagulation and blood residue within the membrane module can be reduced to some extent. However, conventional apparatuses require intermittent rotation of the roller pump, or use of eccentric rollers. Therefore, if such method is to be used with conventional apparatus, a substantial change is required to the existing roller pump. Another problem is that pulse waves produced by the action of the roller pump are of smooth curve pattern and they are therefore absorbed in the circuit, so that the effect of pulsation is decreased.

SUMMARY OF THE INVENTION

It is an object of the present invention to provide an apparatus for producing pulses, which is simple in construction and substantially trouble-free and which can effectively utilize an existing roller pump without any substantial change being required thereof.

It is another object of the invention to provide a pulse-producing apparatus which can produce pulses having a sharp wave pattern, thus assuring satisfactory pulsation effect.

It is another object of the invention to provide a pulse-producing apparatus which can constantly produce pulse waves of constant amplitude.

It is a further object of the invention to provide a pulse-producing apparatus which can readily change the amplitude of pulse waves.

Accordingly, the present invention provides an apparatus for producing pulses, which comprises a roller pump, a membrane module incorporating membranes, a valve for opening and closing a flow path of the liquid being transferred by the pump, start-pressure signalling means for intermittently issuing a close-valve signal to said valve, a synchronous monitor circuit for converting the period of such signal into a voltage value or pulse number, a pressure-period setting circuit for setting a pressure period correlated to the period of said start-pressure signal, and a comparator circuit adapted to continually transmit the close-valve signal until an integrated voltage value or pulse number since the start of pressure application concurs with the monitored value at said monitor circuit.

DETAILED DESCRIPTION OF THE INVENTION

Figure 1:
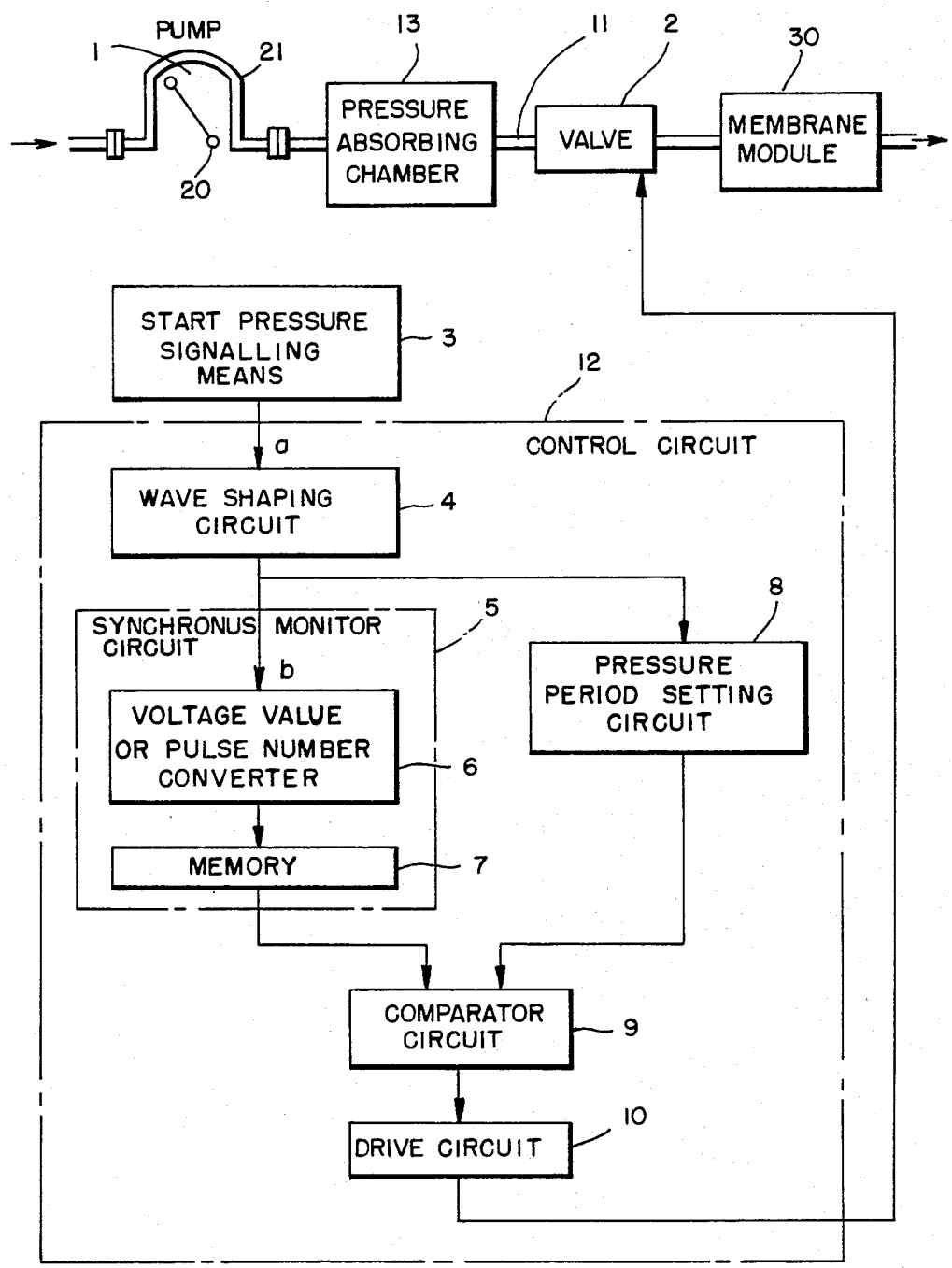
FIG. 1 is a diagram of electric circuits in the apparatus of the present invention.

FIG. 1 is an illustrative representation of the apparatus according to the invention. As shown, the apparatus comprises a roller pump 1, a liquid transfer pipe 11, a membrane module 30, a valve 2, start-pressure signalling means 3, and a control circuit 12 for producing pulses.

The roller pump 1 is such that rollers 20 are pressed against a tube 21 as they move, thereby compressing the tube 21 so that the liquid in the tube is transferred forward in successive order. The number of rollers can be suitably determined according to the required rate of liquid transfer. For the purpose of blood pumping, for example, a 2-roller type roller is normally used.

The liquid transfer pipe 11 may be a stainless-steel pipe or a resin tube, or a flexible plastic tube. A flexible PVC tube is usually employed for transfer of blood or the like. Where such flexible tube is used, the pressure applied to the interior of the tube while the tube is shut off by the valve can be absorbed through inflation of the tube. Where a rigid tube, e.g. a stainless steel tube, is used, however, a prolonged shut-off period may result in pump break-down because the tube has no means to absorb the pressure. Therefore, in the case of a rigid tube being used, it is desirable that a chamber 13 for pressure absorption be provided in the line.

The membrane module 30 incorporates membranes of hollow fiber shape or cylindrical shape or flat plate shape. As is known, such membrane may be of ethylenevinyl alcohol copolymer, cellulose derivative such as cellulose acetate or the like, polyolefin, polyacrylonitrile, polyamide, polyester, or polysulfone. The membranes are housed in the module in a known manner.

The valve 2 attached to the transfer tube is an automatic valve adapted to be automatically opened and closed. When power is switched on, valve 2 closes to disconnect the flow path. Conversely when the apparatus is not in use, or when power is switched off, the flow path is connected. When employed in blood treatment apparatuses, the valve is usually a pinch valve of direct acting type, but for industrial purposes, the valve may be a shut-off valve of some other type, for example, a ball valve or sluice valve. Valve 2 may be attached to the transfer tube 11 on the inlet side or on the outlet side. Usually, it is preferably attached to the transfer tube on the inlet side of the membrane module.

The valve is usually solenoid-operated, but where it is of a large type, the valve may be operated by an air cylinder or electric motor. The valve may be remote controlled through electric or pneumatic signals.

Figure 2:
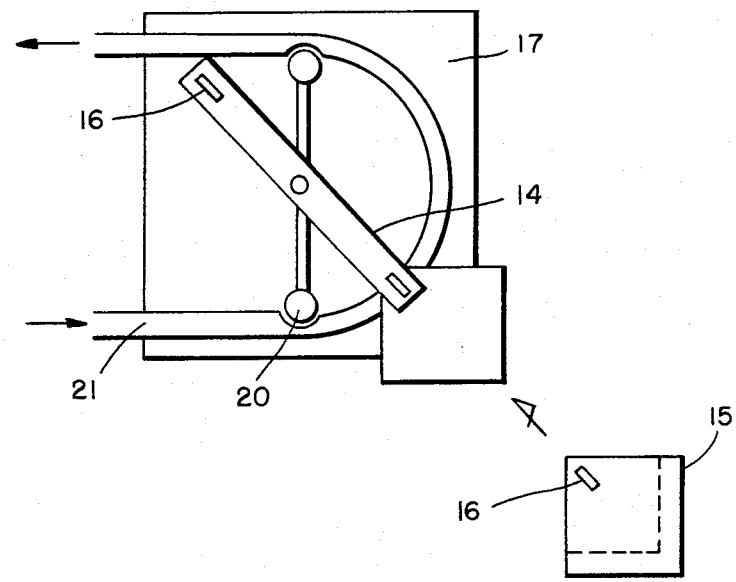
FIG. 2 is a view showing start-pressure signalling means attached to a roller pump.

The start-pressure signalling means 3 transmits to the control circuit 12 a signal for shutting down the valve. As FIG. 2 shows, said signalling means comprises a fixed rotating plate 14 mounted on the rotating shaft of the roller pump 1 and incorporating a magnet 16', and a magnetic proximity switch 16 provided on a movable plate 15 removably attached to a rotary guide of the pump. When the fixed rotating plate 14 rotates to a point just adjacent the proximity switch 16 attached to the movable plate 15, the signalling means is switched on by action of the magnet 16' to transmit a start-pressure signal.

Said signalling means gives a valve-close start signal to the control circuit. Instead of the proximity switch, a phototube or a limit switch may be used. By virtue of the fixed rotating plate fixed to the rotating shaft of the pump, said signalling means gives a pulse (a) which is proportional to the number of pump revolutions, of such form as shown in FIG. 3(1).

The control circuit 12 for pulsation, adapted to set a shut-down period for the valve closed according to the signal from said signalling means 3, comprises a wave shaping circuit 4, a synchronous monitor circuit 5, pressure-period setting circuit 8, a comparator circuit 9, and a drive circuit 10.

Figure 3:
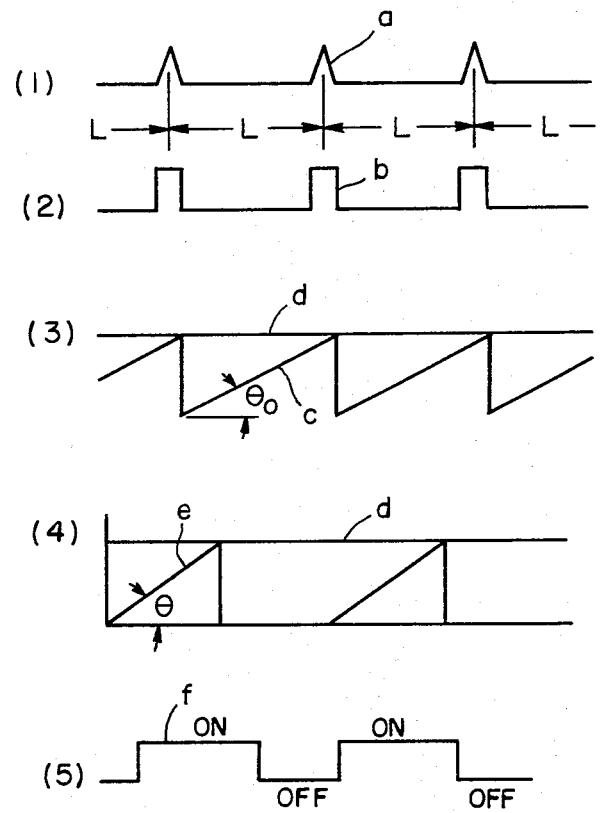
FIG. 3 is a view showing wave patterns which represent respective outputs of the circuits shown in FIG. 1.

In the wave shaping circuit 4, pulses transmitted by said start-pressure signalling means are shaped into such short wave form (b) as shown in FIG. 3(2).

Figure 9:
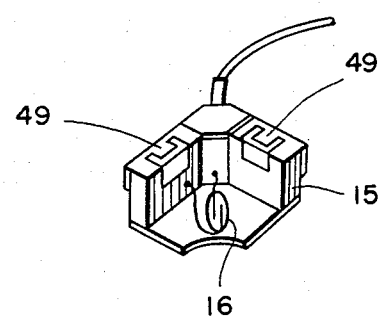
FIG. 9 is a perspective view showing the structure of the movable plate.

An example of a circuit which can be used for wave shaping circuit 4 is provided in FIGS. 3–25, page 53 of the book entitled "How To Use IC", Seiichi Denda, CQ Publishing Co., Sept. 15, 1973. Another example of such a circuit is shown in FIG. 9 of U.S. Pat. No. 4,231,366 as "monoflop" 301.

The synchronous monitor circuit 5 transforms the period of the signal (b) from the wave shaping circuit 4 into a voltage value or pulse number. This circuit 5 comprises an integration circuit for integrating voltage values or pulse numbers, a resetting circuit, a voltage-value or pulse-number conversion circuit 6 for shaping reference waves (c) of sawteeth shape having a ramp inclination of ($\theta_0$), and memory circuit 7 for storing a maximal value (d) of the voltage values or pulse-numbers integrated at said integration circuit. Therefore, if the interval L of pulses (a) is short, or in other words, the rate of pump rotation is large, the interval between reference waves (c) of sawteeth shape having ramp inclination of ($\theta_0$) is short, and the maximal valve (d) of the waves is low. Conversely, if the rate of pump rotation is small, the maximal value (d) of the waves is high.

The ramp voltage produced by voltage-value or pulse-number conversion circuit 6 is obtainable, for example, by the integration circuit shown in FIGS. 3–6, page 108 of "Linear IC Practical Use Handbook", Taihei Ueno, CQ Publishing Co., Dec. 30, 1973. Memory circuit 7 is of conventional design, such as the sample and hold circuit shown in FIGS. 3–25, page 129 of the Linear IC Practical Use Handbook, or that shown in FIG. 8 of U.S. Pat. No. 4,231,366 (sample and hold circuit 203).

The pressure-period setting circuit 8 sets the period of valve shut-off until the pressure of the liquid in the tube reaches a prescribed pressure. This circuit 8 may be constituted of the same circuit that is used as said voltage-value or pulse-number conversion circuit 6. That is, the circuit 8 comprises an integration circuit for integrating voltage values or pulse numbers (e) which tend to become larger at ramp inclination ($\theta$) set by the start-pressure signal, and a resetting circuit. The resetting circuit is provided in common with that of said conversion circuit 6; so, the starting point of voltage-value or pulse-number integration may be the same for the both resetting circuits. The period of pressure application may be set according to the ramp inclination ($\theta$) of the voltage value or pulse value which tends to increase in proportion to time beginning from the point of the start-pressure signal input.

The comparator circuit 9 compares the voltage values or pulse value (e) integrated at ramp inclination ($\theta$) set at the setting circuit 8 with the maximal voltage or pulse value (d) stored at said memory circuit 7, so that a close-valve signal (f) is given to the drive circuit 10 to close the valve for a period until the voltage or pulse value (e) exceeds the stored maximal voltage or pulse value (d). That is, the valve is closed as long as said signal (f) is given, and when such period of close-value signalling ends, the valve is opened and another series of pulses occur, then the valve is closed again.

Such a comparator circuit is described in connection with FIGS. 3–27, pages 130 to 131 of the Linear IC Practical Use Handbook. Another comparator circuit of this nature is shown in FIG. 2 of U.S. Pat. No. Re. 29,346. Drive circuit 10 is also of conventional design such as that shown in FIG. 2 of U.S. Pat. No. Re. 29,346 to actuate relay 104.

Figure 4:
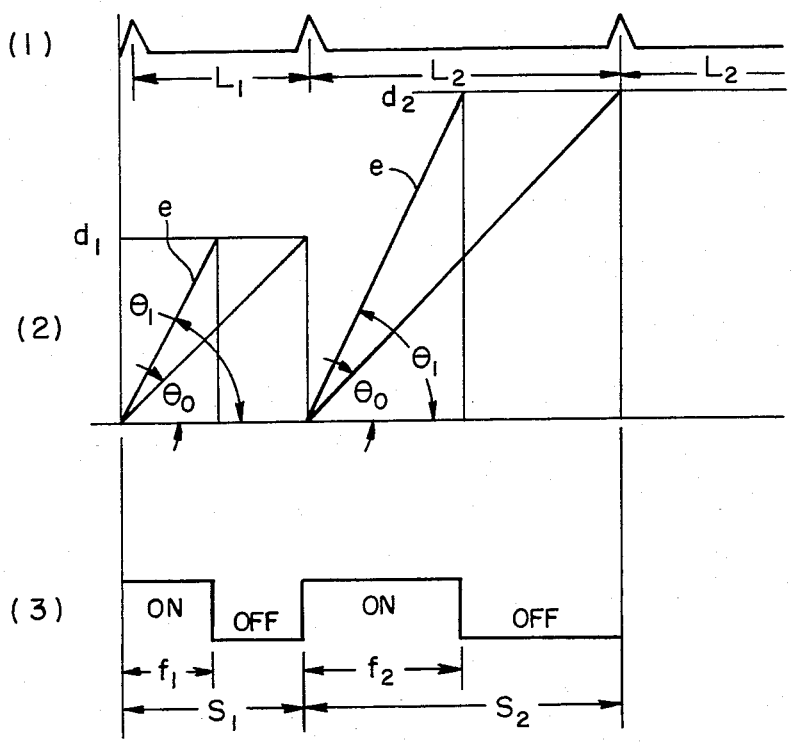
FIG. 4 is a view showing wave patterns which represent the output of the control circuit when the number of revolutions of the pump is varied, with ramp inclination kept constant.

Now, the operation of said control circuit will be explained with reference to FIGS. 4 and 5. FIG. 4 is an illustrative view showing the pattern of operation when the rate of roller-pump run is relatively slow, with ramp inclination kept constant. In this case, the pulse interval is increased from $L_1$ to $L_2$ as FIG. 4(1) shows. Accordingly, the converted voltage or pulse value ($d_2$) is greater than the original converted value ($d_1$), as FIG. 4(2) shows. However, since voltage value or pulse value (e) tends to increase at the set ramp inclination ($\theta_1$), close-valve signals ($f_1$), ($f_2$) are given until said voltage or pulse value (e) concurs with the stored converted values ($d_1$), ($d_2$), as FIG. 4(3) shows. Therefore, between cycles ($s_1$), ($s_2$) and close-valve periods ($f_1$), ($f_2$) the cycles, the following relation holds: $f_1/s_1 = f_2/s_2$. Thus, the period of valve closing in a cycle may always be kept constant irrespective of the run speed of the roller pump. In other words, since the rate of liquid pressure rise (amplitude of pulsation) can always be kept constant, any change in the run speed of the roller pump will not cause an abnormal pressure to be applied to the membrane module, with no damage caused to the membranes; this assures safe operation of the apparatus.

Figure 5:
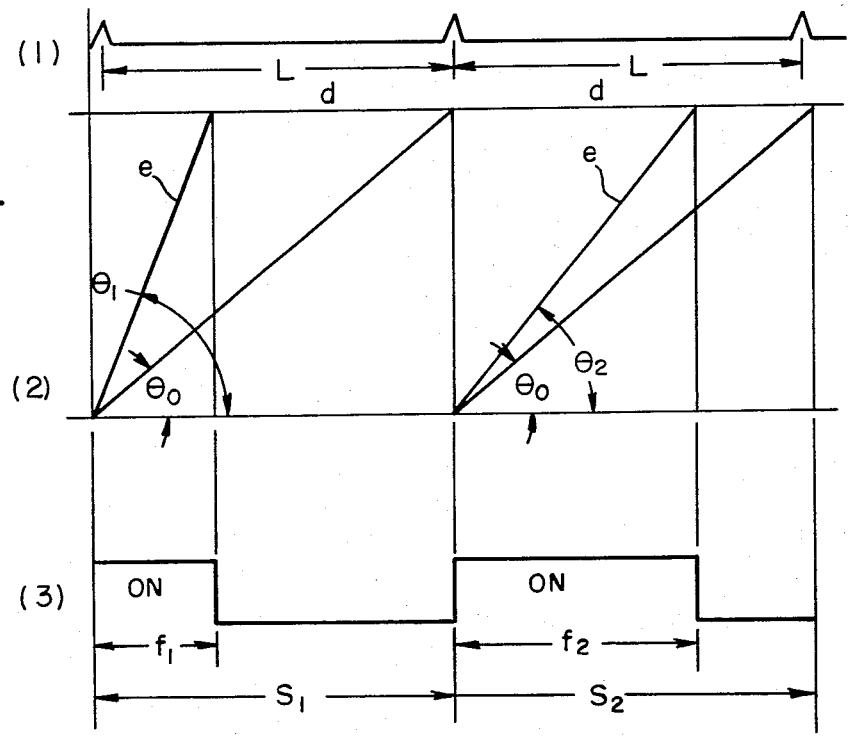
FIG. 5 is a view showing wave patterns which represent the output of the control circuit when the ramp inclination is varied, with the number of pump revolutions kept constant.

Referring to FIG. 5, there is shown a case where the setting of the pressure application period, that is, ramp inclination is changed from ($\theta_1$) to ($\theta_2$) with the run speed of the pump (pulse interval) kept constant at L. In this case, the run speed is constant, and therefore, the maximal converted voltage or pulse value (d) is constant, as FIG. 5(2) shows. As is the case with the former example, close-valve signals ($f_1$), ($f_2$) are given until integrated voltage or pulse values rising with ramp inclination ($\theta_1$) and ($\theta_2$) concur with said maximal converted value (d), as FIG. 5(3) shows. Therefore, if the ramp inclination becomes smaller, the close-valve period is made proportionally longer, that is, from ($f_1$) to ($f_2$), whereby pulses of large amplitude can be produced. Thus, it is possible to suitably select amplitude of pulses by changing the ramp inclination.

Said synchronous monitor circuit, pressure-application period setting circuit, and comparator circuit may incorporate microcomputers.

Figure 6:
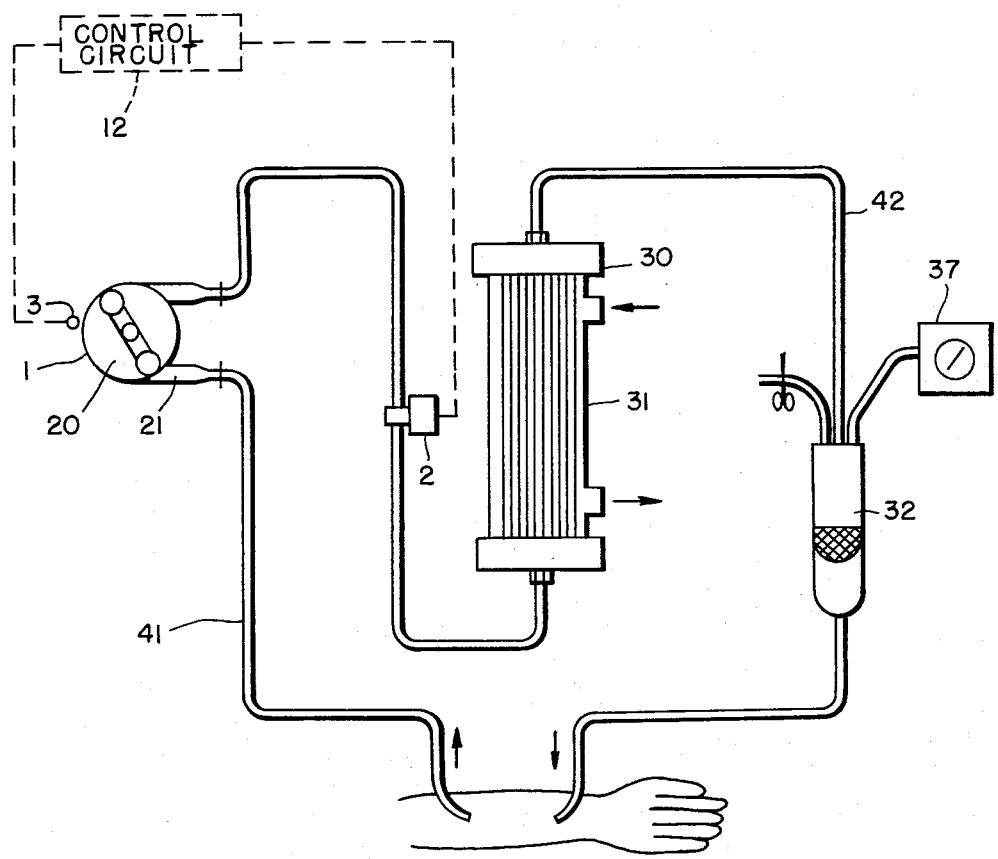
FIG. 6 is a block diagram showing an extracorporeal blood circulating circuit.
Figure 7:
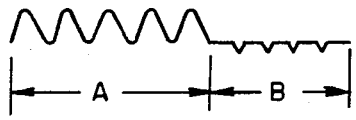
FIG. 7 is a view showing a pulse wave pattern seen where the apparatus of the invention is employed in comparison with that where the apparatus is not employed.

FIG. 6 shows an example in which the apparatus of the invention is applied for the purpose of hemodialysis. As shown, hemodialysis requires an extracorporeal blood circulating circuit such that the blood introduced from a human arterial canal into an artery-side circuit 41 is supplied by means of a roller pump 1 into a membrane module 30 incorporating hollow fibers 31; after metabolized with a dialysate introduced into the module, the blood is returned from a venous-side circuit 42 into the human body via an air chamber 32. Between the roller pump 1 and the membrane module 30 in said circulating circuit there is disposed an automatic pinch valve 2 adapted to be automatically opened and closed. Shown at 37 is a pressure gauge attached to the air chamber. Said pinch valve 2 is such that the open/close period for the valve (that is, amplitude of pulsation) is controlled by start-pressure signalling means 3 attached to the roller pump 1 and a control circuit 12 for setting close-valve period. If the pinch valve 2 is closed, the blood is subjected to pressure between the valve and the roller pump; and after a certain period, if the valve is opened, the blood is supplied into the membrane module 30 under pressure. Therefore, by periodically opening and closing the valve is it possible to produce pulse waves as shown in FIG. 7. In the instance of FIG. 7, the roller pump, of 2-roller type, is run at 20 rpm to supply blood into the membrane module 30 at the rate of 200 ml/hr, with close-valve period set at 0.5 sec. Zone A represents a period during which the valve 2 is closed to produce pulses; and zone B represents a period during which the valve 2 is opened. It is noted that during the zone-B period there is produced a slight degree of pulsation by the roller pump.

Figure 8:
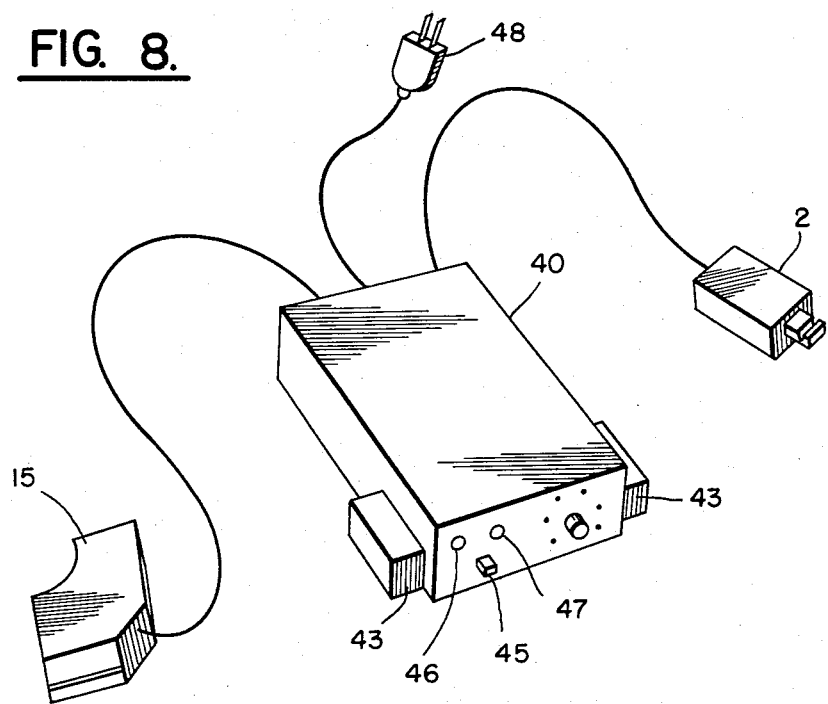
FIG. 8 is a perspective view illustrating a box housing the control circuit and a movable plate and a pinch valve, both connected to the box.
Figure 10:
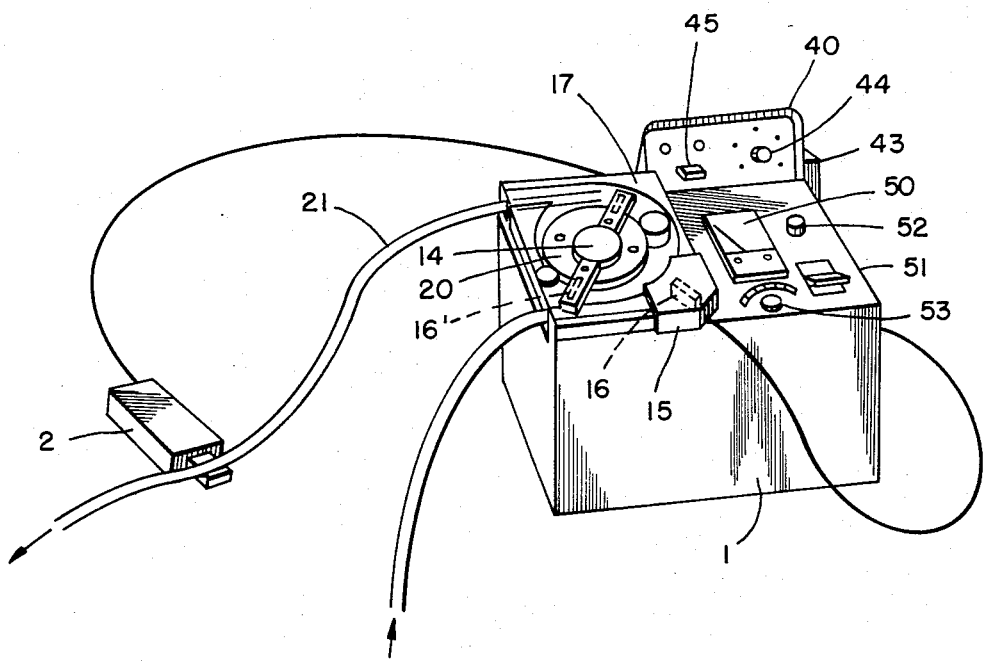
FIG. 10 is a perspective view showing by way of example an arrangement of the invention in which the box and movable plate shown in FIG. 8 are attached to the roller pump, with the pinch valve attached to the blood circuit.

The control circuit 12 is housed in a box shown in FIG. 8. On the front panel of said box there are provided a power switch 45, a power-supply indicator lamp 46, an output indicator lamp 47, and a dial 44 for pressure-application period setting. On both sides of the box there are provided magnets 43 for removably attaching the box to the side wall of the roller pump. At the rear end of the box there are provided a power-supply plug 48, a moving plate 15 attachable to the roller pump, and terminals for connecting lead wires attached to the pinch valve 2. The moving plate 15 to be attached to the roller pump is provided on its interior with a proximity switch 16, as FIG. 9 shows. On side walls of the plate 15 are provided magnets 49, by means of which the plate 15 can be attached to the rotary guide of the roller pump at two corners thereof. FIG. 10 shows an example in which the box 40 with the control circuit housed therein, and the moving plate 15 with the proximity switch 16 housed therein, are attached to the roller pump 1, the box being attached to a side wall of the roller pump through the magnets provided on the side wall of the box. The moving plate 15 is attached to the rotary guide 17 at a corner thereof by means of the magnets. On the rotating shaft of the roller pump there is mounted the fixed rotating plate 14 incorporating magnet 16'. When the magnet 16' disposed the fixed rotating plate 14 reaches a position just under the proximity switch 16 attached to the moving plate 15, a close-valve signal is transmitted to the control circuit, so that the pinch valve 2 by which the blood circuit 41 is grasped is actuated to shut down the blood circuit for a predetermined period. On the top of the roller pump 1 there are disposed an ampere meter 50, a dial 53 for setting runspeed, a power-supply switch 51, and a power indicator lamp 52.

As above described, the apparatus according to the invention is adapted to correlate the run speed of the pump with the period of pressure application, so that the amount of pressure applied can always be maintained constant. At same time, the set valve for the pressure-application period can readily be changed so that any possible danger due to pressure rise can be effectively forestalled. Furthermore, the apparatus of the invention is geared to ease of practical application in such a way that any existing roller pump can be effectively employed in producing pulses, only by attaching start-pressure signalling means thereto. Another advantage is that the apparatus in simple in construction, substantially trouble-free, and low in cost.

Although, the apparatus has been described with respect to the application thereof for hemodialysis purposes, it is clear from the foregoing description that the present invention can be employed for other purposes than hemodialysis, through a roller-pump/membrane-module combination.

What is claimed is:

1. Apparatus for producing a controlled pulsed liquid flow comprising:
   a roller pump for pumping a liquid;
   a conduit coupled to the output of said pump for providing a liquid flow path;
   a normally open valve coupled to said flow path for closing the flow path in response to a close-valve signal;
   start-pressure signalling means operatively associated with said pump for intermittently issuing a start-pressure signal;
   synchronous monitor circuit means for generating a voltage value or pulse number representative of the period of said start-pressure signal;
   pressure-period setting circuit means for generating a time varying signal in accordance with a desired pressure-period setting and in correlation with the period of said start-pressure signal; and
   comparator circuit means coupled to said synchronous monitor circuit means and said pressure-period setting circuit means for comparing said time varying signal to the voltage value or pulse number generated by said synchronous monitor circuit means, and producing a close-valve signal commencing with the issuance of said start-pressure signal and terminating when the value of said time varying signal concurs with said voltage value or pulse number.

2. The apparatus of claim 1 wherein said time varying signal is a ramp of increasing amplitude having a slope determined by said desired pressure-period setting.

3. The apparatus of claim 1 further comprising a membrane module coupled to said flow path.

4. The apparatus of claim 1 wherein said start-pressure signaling means cmprises a fixed rotating plate mounted on a rotating shaft of the roller pump and having magnets provided thereon, and a proximity switch provided on a plate removably attached to a rotary guide of the pump.

5. The apparatus of claim 1 wherein said normally open valve for opening and closing said flow path is a pinch valve.

6. The apparatus of claim 1 wherein said synchronous monitor circuit comprises a converter circuit for converting the period of said start-pressure signal into a voltage value or pulse number, and a memory circuit for storing a maximal value of said voltage value or pulse number.

* * * * *